United States Patent
Shirai et al.

(10) Patent No.: US 6,573,397 B2
(45) Date of Patent: Jun. 3, 2003

(54) PROCESS FOR PRODUCING 3,4-DIHYDROXYBENZONITRILE

(75) Inventors: Masashi Shirai, Ube (JP); Koji Shiba, Ube (JP); Toshio Furuya, Ube (JP)

(73) Assignee: Ube Industries, Ltd., Yamaguchi-ken (JP)

( * ) Notice: Subject to any disclaimer, the term of this patent is extended or adjusted under 35 U.S.C. 154(b) by 0 days.

(21) Appl. No.: 10/170,360

(22) Filed: Jun. 14, 2002

(65) Prior Publication Data

US 2003/0009048 A1 Jan. 9, 2003

(30) Foreign Application Priority Data

Jun. 19, 2001 (JP) ........................................ 2001-184399
Jun. 19, 2001 (JP) ........................................ 2001-184400

(51) Int. Cl.[7] ............................................. C07C 255/50
(52) U.S. Cl. ........................................ 558/423; 549/434
(58) Field of Search ........................... 558/423; 549/434

(56) References Cited

PUBLICATIONS

Hwu, Jih Ru et al: "Sodium Bis (trimethylsilyl) amide and Lithium Diisopropylamide in Deprotection of Alkyl Aryl Ethers:.alpha.–Effect of Silicon" Journal of Organic Chemistry (1997), 62(12), 4097–4104, 1997, XP002207147 * p. 4101 *.

Cassels, Bruce K. et al: "Regioselective ring opening by propanethiolate of (methylenedioxy)benzenes with electron-–withdrawing substituents" Recl. Trav. Chim. PAYS–BAS (1992), 111(10), 448–450, 1992, XP001074119 * p. 448 –p. 449 *.

*Primary Examiner*—Joseph K. McKane
*Assistant Examiner*—Kamal Saeed
(74) *Attorney, Agent, or Firm*—Arent Fox Kintner Plotkin & Kahn, PLLC

(57) ABSTRACT

3,4-dihydroxybenzonitrile useful as a starting compound for synthesis of medicines and agricultural chemicals is produced, with a high yield by chlorinating 3,4-methylenedioxybenzonitrile with sulfuryl chloride or a mixture of molecular chlorine with a chlorination-promoter including phosphorus trichloride, phosphorus pentachloride, sulfuryl chloride, thionyl chloride, and/or nitrosyl chloride, to prepare 2-chloro-benzo[1,3]dioxole-5-carbonitrile, and hydrolyzing 2-chloro-benzo[1,3]dioxole-5-carbonitrile by contacting it with water to produce 3,4-dihydroxybenzonitrile.

12 Claims, No Drawings

PROCESS FOR PRODUCING 3,4-DIHYDROXYBENZONITRILE

TECHNICAL FIELD

The present invention relates to a process for producing 3,4-dihydroxybenzonitrile. More particularly, the present invention relates to a process for producing 3,4-dihydroxybenzonitrile from 3,4-methylenedioxybenzonitrile.

The target 3,4-dihydroxybenzonitrile is useful as a starting material for synthesis of medicines or agricultural chemicals, particularly for synthesis of quinazoline compounds usable as an anticancer agent.

BACKGROUND ART

As a conventional process for producing 3,4-dihydroxybenzonitrile from 3,4-methylenedioxybenzonitrile, for example, J. Org. Chem., 62, 4097 (1977) discloses a process in which 3,4-methylenedioxybenzonitrile is reacted with lithium diisopropylamide in an excess molar amount (five times by mole or more) in a reaction medium consisting of 1,3-dimethyl-2-imidazolidinone at a high temperature of 185° C., to produce 3,4-dihydroxybenzonitrile with a yield of 94%. This process is, however, disadvantageous as an industrial process in that lithium diisopropylamide, which has a high ignition property, must be employed, and the reaction conditions are very severe and a complicated after-treatment is necessary.

DISCLOSURE OF THE INVENTION

An object of the present invention is to provide a process for producing 3,4-dihydroxybenzonitrile with a high yield from 3,4-methylenedioxybenzonitrile by simple and easy procedures suitable for industrial practice.

The above-mentioned object can be attained by the process of the present invention for producing 3,4-dihydroxybenzonitrile, which comprises the steps of:

chlorinating 3,4-methylenedioxybenzonitrile with at least one member selected from the group consisting of sulfuryl chloride and mixtures of molecular chlorine with a chlorination-promoter consisting of at least one member selected from phosphorus trichloride, phosphorus pentachloride, sulfuryl chloride, thionyl chloride, and nitrosyl chloride, to prepare 2-chloro-benzo[1,3]dioxole-5-carbonitrile, and hydrolyzing 2-chloro-benzo[1,3]dioxole-5-carbonitrile by contacting it with water to produce 3,4-dihydroxybenzonitrile.

In the process of the present invention, the chlorination procedure is preferably carried out in a reaction medium comprising at least one chlorination-resistive solvent.

Also, in the process of the present invention, the reaction medium for the chlorination procedure is preferably present in an amount of 1 to 50 ml per g of 3,4-methylenedioxybenzonitrile.

Additionally, in the process of the present invention, the chlorination procedure is preferably carried out at a temperature of 5 to 150° C.

Further, in the process of the present invention, the chlorination procedure using the molecular chlorine-chlorination promoter mixture, a chlorination reaction mixture is preferably prepared by introducing a molecular chlorine gas into a mixture of 3,4-methylenedioxybenzonitrile with the chlorination-promoter.

Yet further, in the process of the present invention, the molecular chlorine in the chlorination reaction mixture is preferably present in an amount of 1 to 50 moles per mole of 3,4-methylenedioxybenzonitrile.

Still further, in the process of the present invention, the chlorination promoter in the chlorination reaction mixture is preferably present in an amount of 0.05 to 5 moles per mole of 3,4-methylenedioxybenzonitrile.

Moreover, in the process of the present invention, the chlorination procedure is preferably carried out by using sulfuryl chloride in an amount of 1 to 50 moles per mole of 3,4-methylenedioxybenzonitrile.

In addition, in the process of the present invention, the chlorination procedure with sulfuryl chloride is preferably carried out in an inert gas atmosphere under a gauge pressure of 0 to 1000 kPa at a temperature of 5 to 100° C.

Furthermore, in the process of the present invention, the hydrolysis procedure is preferably carried out at a temperature of 5 to 100° C.

Finally, in the process of the present invention, the hydrolysis procedure, water is preferably present in an amount of 1 to 50 g per g of 3,4-methylenedioxybenzonitrile.

The process of the present invention optionally comprises a step of collecting the resultant 3,4-dihydroxybenzonitrile from the reaction mixture of hydrolysis procedure by at least one procedure selected from precipitation, recrystallization, distillation and column chromatography.

BEST MODE OF CARRYING OUT THE INVENTION

In the first step of the process of the present invention for producing 3,4-dihydroxybenzonitrile, a starting compound, namely 3,4-methylenedioxybenzonitrile represented by the formula (1):

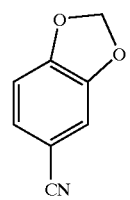

(1)

is chlorinated with at least one member selected from the group consisting of (A) sulfuryl chloride and (B) mixtures of (a) molecular chlorine with (b) a chlorination-promoter consisting of at least one member selected from phosphorus trichloride, phosphorus pentachloride, sulfuryl chloride, thionyl chloride and nitrosyl chloride, to produce an 2-chloro-benzo[1,3]dioxole-5-carbonitrile represented by the formula (2):

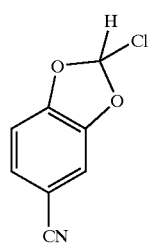

(2)

In the next step, the reaction mixture discharged from the chlorination step and containing the resultant 2-chlorobenzo[1,3]dioxole-5-carbonitrile is brought into contact with water to hydrolyze this compound into 3,4-dihydroxybenzonitrile represented by the formula (3):

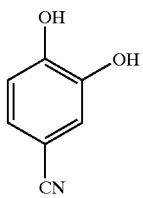
(3)

The 2-chloro-benzo[1,3]dioxole-5-carbonitrile of the formula (2) is a novel compound prepared for the first time by the present invention.

In an embodiment (1) of the process of the present invention, the chlorination of 3,4-methylenedioxybenzonitrile is carried out by using, as a chlorination agent, a mixture of molecular chlorine with a chlorination promoter.

The chlorination promoter consists of at least one member selected from the group consisting of phosphorus trichloride, phosphorus pentachloride, sulfuryl chloride, thionyl chloride ($SOCl_2$) and nitrosyl chloride (NOCl), preferably phosphorus trichloride and phosphorus pentachloride. The above-mentioned compounds for the chlorination promoter can be employed alone or in a mixture of two or more thereof.

In this embodiment (1), the molecular chlorine is preferably employed in an amount of 1 to 50 moles, more preferably 1 to 10 moles, per mole of 3,4-methylenedioxybenzonitrile, and the chlorination promoter is preferably employed in an amount of 0.05 to 5 moles, more preferably 0.1 to 2 moles per mole of 3,4-methylenedioxybenzonitrile.

In the embodiment (1), the chlorination procedure is preferably carried out in a reaction liquid medium. There is no limitation to the type of compounds usable for the reaction liquid medium, as long as the compounds do not hinder the chlorination reaction of 3,4-methylenedioxybenzonitrile and are resistive to chlorination with the mixture of the molecular chlorine with the chlorination promoter.

The reaction liquid medium preferably comprises, as a main component, at least one member selected from aromatic hydrocarbons, for example, benzene, toluene, xylene, ethylbenzene, tert-butylbenzene; halogenated aromatic hydrocarbons, for example, chlorobenzene; aliphatic hydrocarbons, for example, n-hexane, n-heptane, n-octane, n-decane, cyclohexane, cycloheptane, cyclooctane; halogenated aliphatic hydrocarbons, for example, methylenechloride, chloroform, tetrachloromethane, and dichloroethane; ethers, for example, diethylether, diisopropylether, tetrahydrofuran, and dioxane; and carboxylate esters, for example ethyl acetate, and butyl acetate. Preferably, the aromatic hydrocarbons, halogenated aromatic hydrocarbons, and carboxylate esters, more preferably, the aromatic hydrocarbons, and carboxylate esters are employed for the reaction liquid medium. These compounds for the reaction liquid medium may be employed alone or in a mixture of two or more thereof.

The amount of the reaction medium is controlled, in consideration of the uniformity of the reaction mixture and ease of stirring the reaction mixture, in preferably 1 to 50 ml, more preferably 2 to 20 ml per g of 3,4-methylenedioxybenzonitrile in the reaction mixture.

In the chlorination step of the embodiment (1) of the process of the present invention, 3,4-methylenedioxybenzonitrile is mixed with a chlorination promoter and preferably a reaction liquid medium, then a chlorine gas (as a molecular chlorine), which may be diluted with an inert gas, for example, nitrogen or argon gas, is introduced into the 3,4-methylenedioxybenzonitrile-containing mixture, while the resultant reaction mixture is stirred. In this step, the reaction temperature is preferably adjusted to 5 to 150° C., more preferably 25 to 100° C. There is no limitation to the reaction pressure or the feed (introduction) rate of the chlorine gas.

In the other embodiment (2) of the process of the present invention, the chlorination of 3,4-methylenedioxybenzonitrile is carried out by using, as a chlorination agent, sulfuryl chloride ($SO_2Cl_2$).

Also, in the embodiment (2), sulfuryl chloride is preferably employed in an amount of 1 to 50 moles, more preferably 1 to 10 moles, per mole of the starting compound, 3,4-methylenedioxybenzonitrile.

Further, in the embodiment (2), the chlorination procedure is preferably carried out in a reaction liquid medium. There is no limitation to the type of compounds from which the reaction liquid medium is prepared, as long as the compounds do not hinder the chlorination reaction of 3,4-methylenedioxybenzonitrile and are resistive to chlorination with sulfuryl chloride. The reaction liquid medium preferably comprises, as a main component, at least one member selected from the same compounds usable for the embodiment (1).

The reaction liquid medium is preferably used in an amount which is variable in response to the uniformity and ease of stirring the resultant reaction mixture, of 1 to 50 ml, more preferably 2 to 20 ml, per g of 3,4-methylenedioxybenzonitrile.

In addition, in the embodiment (2), the chlorination step is carried out by mixing 3,4-methylenedioxybenzonitrile with sulfuryl chloride and the reaction liquid medium, while the resultant reaction mixture is stirred. In this case, the reaction temperature is preferably 5 to 150° C., more preferably 25 to 100° C. The reaction pressure may be ambient atmospheric pressure.

To enhance the chlorination reaction rate, the chlorination with sulfuryl chloride is preferably carried out in an inert gas atmosphere under a gauge pressure of 0 to 1000 kPa, more preferably 1 to 100 kPa, at a temperature of 5 to 100° C., more preferably 25 to 70° C. The inert gas preferably comprises at least one member selected from nitrogen or argon.

As a result of the chlorination step, 2-chloro-benzo[1,3]dioxole-5-carbonitrile is produced as a main product and contained in the resultant reaction mixture. The reaction mixture is usually subjected directly to the hydrolysis step. Optionally, the reaction mixture discharged from the chlorination step is subjected to a concentration procedure of 2-chloro-benzo[1,3]dioxole-5-carbonitrile, and then the concentrated reaction mixture is subjected to the hydrolysis step. Alternatively, the reaction mixture is subjected to an isolation procedure of 2-chloro-benzo[1,3]dioxole-5-carbonitrile, by precipitation, recrystallization, distillation, column chromatography, the like, and then the isolated 2-chloro-benzo[1,3]dioxole-5-carbonitrile is subjected to the hydrolysis step.

In the hydrolysis step, 2-chloro-benzo[1,3]dioxole-5-carbonitrile prepared by the chlorination step is hydrolyzed to produce 3,4-dihydroxybenzonitrile. This hydrolysis step may be carried out under conventional hydrolysis conditions. When the reaction mixture discharged from the chlorination step and containing 2-chloro-benzo[1,3]dioxole-5-carbonitrile is fed directly or after being concentrated, into the hydrolysis step, only water, which may be cold water or ice water, is added to the reaction mixture or the concentrated reaction mixture. In this case, the reaction system is preferably in an acid condition. When 2-chloro-benzo[1,3]dioxole-5-carbonitrile is isolated, water and an acid are mixed with the isolated 2-chloro-benzo[1,3]dioxole-5-carbonitrile. Specifically, in this case, the hydrolysis reaction is carried out in an acid condition.

The amount of water to be added to the hydrolysis reaction system is variable in response to the uniformity and ease of stirring the reaction system, and preferably 1 to 50 g, more preferably 2 to 20 g per g of the starting compound, namely 3,4-methylenedioxybenzonitrile.

The hydrolysis step of the process of the present invention can be carried out by mixing water into the reaction mixture discharged from the chlorination step or the concentrated reaction mixture, or with the isolated 2-chloro-benzo[1,3]dioxole-5-carbonitrile, at an acid condition, in an inert gas atmosphere, while the reaction system is stirred. The hydrolysis reaction is preferably carried out at a reaction temperature of 5 to 100° C., more preferably 25 to 70° C., for 15 to 90 minutes. There is no limitation to the reaction pressure. The inert gas preferably comprises nitrogen or argon.

After the hydrolysis reaction is completed, the resultant 3,4-dihydroxybenzonitrile is separated from the reaction mixture and purified by a conventional separation and purification method, for example, precipitation, recrystallization, distillation and column chromatography.

EXAMPLES

The present invention will be further illustrated by the following examples which are not intended to restrict the scope of the present invention in any way.

Referential Example

Production of 2-chloro-benzo[1,3]dioxole-5-carbonitrile

A flask having an inside volume of 50 ml and equipped with a stirrer, a thermometer, a dropping funnel and a gas-introduction pipe was charged with 5.00 g (34.0 milli moles) of 3,4-methylenedioxybenzonitrile and 25 ml of benzene in a nitrogen gas atmosphere. Then, while the resultant mixture was stirred in the flask, 0.47 g (3.4 m moles) of phosphorus trichloride was added into the mixture via the dropping funnel. The resultant mixture was heated to a temperature of 50° C., and then chlorine gas was successively introduced into the mixture through a gas-introduction pipe over a period of 3 hours, at the above-mentioned temperature.

After the chlorination reaction was completed, the resultant reaction mixture was concentrated under a reduced pressure at a temperature of 50° C. to remove benzene. The target compound, 2-chloro-benzo[1,3]dioxole-5-carbonitrile in the state of orange-colored crystals was obtained in an amount of 5.90 g with an isolation yield of 96% by mole.

The results of CI-MS (mass spectrometric analysis) and $^1$H-NMR (nuclear magnetic resonance analysis) are shown below.

CI-MS (m/e): 182 (MH$^+$) $^1$H-NMR ($C_6D_6$, δ (ppm)): 6.07 (1H, d, J=8.06 Hz), 6.29 (1H, d, J=1.71 Hz), 6.45 (1H, dd, J=1.71, 8.06 Hz), 6.99 (1H, s)

The 2-chloro-benzo[1,3]dioxole-5-carbonitrile is a novel compound.

Example 1

A flask having an inside volume of 200 ml and equipped with a stirrer, a thermometer, a dropping funnel and a gas-introduction pipe was charged with 10.00 g (67.97 milli moles) of 3,4-methylenedioxybenzonitrile and 50 ml of toluene in a nitrogen gas atmosphere. Then, while the resultant mixture is stirred in the flask, 0.96 g (6.99 milli moles) of phosphorus trichloride was added into the mixture via the dropping funnel. The resultant mixture was heated to a temperature of 50° C., and then chlorine gas was successively introduced into the mixture through the gas-introduction pipe over a period of 3.5 hours, at the above-mentioned temperature.

After the chlorination reaction was completed, the resultant reaction mixture was cooled to room temperature and concentrated under a reduced pressure to remove toluene.

Then, the concentrated reaction mixture was mixed with 50 ml of water, and the resultant reaction system was heated to a temperature of 50° C. and stirred at the above-mentioned temperature for 30 minutes. After the hydrolysis reaction was completed, the reaction system was cooled to a temperature of 5° C. and further stirred at this temperature for one hour. The resultant precipitated crystals were collected by filtration, washed with water and dried at a temperature of 50° C. under a reduced pressure. 3,4-dihydroxybenzonitrile in the state of white-colored crystals was obtained in an amount of 8.41 g (isolation yield of 92%).

Examples 2 to 5

In each of Examples 2 to 5, 3,4-dihydroxybenzonitrile was produced by the same procedures as in Example 1, except that benzene used as a reaction medium was replaced by the compound as shown in Table 1, and the chlorination reaction time was changed as shown in Table 1.

The conversion of 3,4-methylenedioxybenzonitrile (MDBN) and selectivity to 3,4-dihydroxybenzonitrile (DHBN) was determined from the results of high performance liquid chromatographic analysis (absolute calibration curve method) of the resultant product. The results are shown in Table 1.

TABLE 1

| Example No. | Reaction medium | Reaction time (h) | Conversion of MDBN (mol. %) | Selectivity to DNBN (mol. %) |
| --- | --- | --- | --- | --- |
| 2 | Xylene | 1 | 99 | 96 |
| 3 | tert-Butylbenzene | 1 | 99 | 88 |
| 4 | Ethyl acetate | 4 | 91 | 81 |
| 5 | Benzene | 2 | 100 | 89 |

[Note]
MDBN . . . 3,4-methylenedioxybenzonitrile
DHBN . . . 3,4-dihydroxybenzonitrile Example 6

An glass flask having an inside volume of 25 ml and equipped with a stirrer, a thermometer and a dropping funnel was charged, in a nitrogen gas atmosphere, with 1.00 g (6.8 milli moles) of 3,4-methylenedioxybenzonitrile and 5 ml of toluene. The mixture was heated to a temperature of 50° C. while being stirred, and then 3.67 g (27.2 milli mole) of sulfuryl chloride were gradually mixed into the heated mixture. The resultant reaction mixture was stirred at a temperature of 50° C. for 8 hours to chlorinate 3,4-methylenedioxybenzonitrile After the chlorination reaction was completed, the resultant reaction mixture containing the chlorination product was mixed with 15 g of ice water, and heated to a temperature of 50° C. and a hydrolysis reaction of the chlorination product was carried out at this temperature for one hour.

After the hydrolysis reaction was completed, the resultant reaction mixture was mixed with 250 ml of acetonitrile to provide a homogenous solution. The solution was subjected to a high performance liquid chromatographic analysis (absolute calibration curve method). As a result, it was confirmed that the conversion of 3,4-methylenedioxybenzonitrile was 78% by mole and the selectivity to 3,4-dihydroxybenzonitrile was 90% by mole.

Example 7

A glass autoclave having an inside volume of 100 ml and equipped with a stirrer was charged with 1.00 g (6.8 milli moles) of 3,4-methylenedioxybenzonitrile, 3.67 g (27.2 milli mole) of sulfuryl chloride and 5 ml of toluene. The inside of the autoclave was filled with nitrogen gas under a gauge pressure of 150 kPa, and the charged mixture was heated at a temperature of 50° C. for 3 hours, while being stirred, to chlorinate 3,4-methylenedioxybenzonitrile.

After the chlorination reaction was completed, the resultant reaction mixture containing the chlorination product was mixed with 15 g of ice water, and heated to a temperature of 50° C. and a hydrolysis reaction of the chlorination product was carried out at this temperature for one hour.

After the hydrolysis reaction was completed, the resultant reaction mixture was mixed with 250 ml of acetonitrile to provide a homogenous solution. The solution was subjected to a high performance liquid chromatographic analysis (absolute calibration curve method). As a result, it was confirmed that the conversion of 3,4-methylenedioxybenzonitrile was 73% by mole and the selectivity to 3,4-dihydroxybenzonitrile was 92% by mole.

INDUSTRIAL APPLICABILITY

The process of the present invention enables 3,4-dihydroxybenzonitrile to be produced from 3,4-methylenedioxybenzonitrile, at a high yield and is applicable to industrial practice.

What is claimed is:

1. A process for producing 3,4-dihydroxybenzonitrile comprising the steps of:

chlorinating 3,4-methylenedioxybenzonitrile with at least one member selected from the group consisting of sulfuryl chloride and mixtures of molecular chlorine with a chlorination-promoter consisting of at least one member selected from phosphorus trichloride, phosphorus pentachloride, sulfuryl chloride, thionyl chloride, and nitrosyl chloride, to prepare 2-chloro-benzo[1,3]dioxole-5-carbonitrile, and hydrolyzing 2-chloro-benzo[1,3]dioxole-5-carbonitrile by contacting it with water to produce 3,4-dihydroxybenzonitrile.

2. The process as claimed in claim 1, wherein the chlorination procedure is carried out in a reaction medium comprising at least one chlorination-resistive solvent.

3. The process as claimed in claim 2, wherein the reaction medium for the chlorination procedure is present in an amount of 1 to 50 ml per g of 3,4-methylenedioxybenzonitrile.

4. The process as claimed in claim 1, wherein the chlorination procedure is carried out at a temperature of 5 to 150° C.

5. The process as claimed in claim 1, wherein in the chlorination procedure using the mixture of molecular chlorine with the chlorination promoter, a chlorination reaction mixture is prepared by introducing molecular chlorine gas into a mixture of 3,4-methylenedioxybenzonitrile with the chlorination-promoter.

6. The process as claimed in claim 5, wherein in the chlorination reaction mixture, the molecular chlorine is present in an amount of 1 to 50 moles per mole of 3,4-methylenedioxybenzonitrile.

7. The process as claimed in claim 5, wherein in the chlorination reaction mixture, the chlorination promoter is present in an amount of 0.05 to 5 moles per mole of 3,4-methylenedioxybenzonitrile.

8. The process as claimed in claim 1, wherein the chlorination procedure is carried out by using sulfuryl chloride in an amount of 1 to 50 moles per mole of 3,4-methylenedioxybenzonitrile.

9. The process as claimed in claim 8, wherein the chlorination procedure with sulfuryl chloride is carried out in an inert gas atmosphere under a gauge pressure of 0 to 1000 kPa at a temperature of 5 to 100° C.

10. The process as claimed in claim 1, wherein the hydrolysis procedure is carried out at a temperature of 5 to 100° C.

11. The process as claimed in claim 1, wherein in the hydrolysis procedure, water is present in an amount of 1 to 50 g per g of 3,4-methylenedioxybenzonitrile.

12. The process as claimed in claim 1, further comprising a step of collecting the resultant 3,4-dihydroxybenzonitrile from the reaction mixture of hydrolysis procedure by at least one procedure selected from precipitation, recrystallization, distillation and column chromatography.

* * * * *